United States Patent
Davila

(10) Patent No.: US 7,141,025 B2
(45) Date of Patent: Nov. 28, 2006

(54) APPARATUS AND METHOD FOR QUALITATIVE ASSESSMENT OF PELVIC FLOOR MUSCULAR STRENGTH

(76) Inventor: Guillermo Hernan Davila, 2580 SE. 8th St., Pompano Beach, FL (US) 33062

( * ) Notice: Subject to any disclaimer, the term of this patent is extended or adjusted under 35 U.S.C. 154(b) by 251 days.

(21) Appl. No.: 10/307,544

(22) Filed: Nov. 29, 2002

(65) Prior Publication Data

US 2004/0106879 A1 Jun. 3, 2004

(51) Int. Cl.
*A61B 5/103* (2006.01)
(52) U.S. Cl. .................... 600/591; 600/587; 73/379.01
(58) Field of Classification Search ................ 600/587, 600/591, 38, 41; 604/500; 482/92–96, 131; 73/379.01; 128/897, 898
See application file for complete search history.

(56) References Cited

U.S. PATENT DOCUMENTS

| | | | | |
|---|---|---|---|---|
| 3,726,273 A | * | 4/1973 | Cole | 600/591 |
| 3,900,953 A | * | 8/1975 | Posen | 433/72 |
| 4,721,507 A | * | 1/1988 | Chin | 604/100.02 |
| 4,936,399 A | * | 6/1990 | Christman et al. | 177/210 C |
| 5,407,412 A | * | 4/1995 | Plevnik et al. | 482/105 |
| 5,483,832 A | * | 1/1996 | Pauser et al. | 73/379.08 |
| 5,733,230 A | * | 3/1998 | Sawchuck et al. | 482/111 |
| 5,747,688 A | * | 5/1998 | Krementsov | 73/379.01 |
| 6,068,581 A | * | 5/2000 | Anderson | 482/93 |
| 6,406,411 B1 | * | 6/2002 | Guagliano et al. | 482/121 |
| 6,562,018 B1 | * | 5/2003 | Russell | 604/500 |
| 6,672,996 B1 | * | 1/2004 | Ross et al. | 482/121 |

* cited by examiner

Primary Examiner—Charles Marmor
(74) Attorney, Agent, or Firm—Patent Pro

(57) ABSTRACT

An apparatus and method for qualitative assessment of pelvic floor muscular strength includes inserting a spherical intracavitary device into vagina or anus above the level of the levator plate and measuring a force necessary to remove the inserted device from the vagina or anus. A diagnostic set for qualitative assessment of pelvic floor muscular strength, includes at least one spherical intracavitary device and a force gauge. The device and force gauge can be attached together after insertion of the device into the vagina or anus.

8 Claims, 1 Drawing Sheet

APPARATUS AND METHOD FOR QUALITATIVE ASSESSMENT OF PELVIC FLOOR MUSCULAR STRENGTH

BACKGROUND OF THE INVENTION

The invention relates to pelvic floor strength, and in particular an apparatus and method for qualitative assessment of pelvic floor muscular strength.

Pelvic floor weakness is a critical factor in the development of such dysfunctions like stress urinary incontinence, genital prolapse, and fecal incontinence. Accurate pelvic floor functional assessment is important when determining the degree of dysfunction, the amenability of the dysfunction to non-surgical therapy, and for monitoring the success of treatment. Multiple methods of pelvic floor strength assessment have been developed. Worth, Dougherty and McKey, Nurs. Res., 1986:35 and Brink et al., Nurs. Res., 1989:38 describe a method using digital pelvic assessment (DPA) scales; Bo and Kerschan-Schindl et al, Neurourol. Urodyn., 1992: and 2002:21, respectively, describe a method using vaginal pressure measurements; Jonasson et al., Acta Obstet. Gynecol. Scand. 1989:68 and Contreras and Coya, Int. Urogynecol J. 1996:7 describe the use of vaginal cones; Weidner, Barber et al, and Weidner, Sanders et al, Am. J. Obstet. Gynecol., 2000:183, respectively, describe the use of electromyographic activity measurement (EMG). However, Worth et al, Bo, Hahn et al., Gynecol. Obstet. Invest. 1996:41, Peschers et al. Int. Urogynecol. J. 2001:12 and Bo and Finckenhagen, Acta Obstet. Gynecol. Scand. 2001:80 have shown these methods to have disadvantages, such as subjective and indirect measurement, cumbersome data collection, measurement artifacts, or prohibitive cost for routine office use. In addition, the DPA is not designed to assess resting pelvic tone. Because it is the dynamic action of the muscles that is believed to prevent dysfunction, any static state measure may be a poor representation and of limited clinical utility.

Accurate assessment of pelvic floor muscle function has remained difficult to achieve. Previously described techniques have been limited by providing only indirect and subjective information on pelvic contractions in the form of generated vaginal pressure. The exceptions may be an instrumented vaginal speculum force gauge developed at the University of Michigan by Sampselle et al., Obstet. Gynecol. 1998:91 that is not commercially available and vaginal cones. However, the speculum also measures circumferential pressure, not retentive force.

Kerschan-Schindl et al. and Hahn et al. have shown pressure perineometry, a widely used technique, to be a reproducible method of measuring vaginal pressure in both continent and incontinent women. However, this instrument is limited in that it measures all pressure changes in the vagina. Contraction of the rectus abdominus and/or adductor muscles, in addition to the pelvic floor muscles, will result in increased pressure recordings. Further, most electronic pressure devices have a narrow sensor area, making placement a problem.

Perineometry using EMG activity is another commonly used method. Again, this method is limited because it is indirect and the origin of the potentials generated cannot be localized to the pelvic floor muscles. Previous studies by Peschers et al. demonstrated that adductor muscle activity increases EMG recordings. Additionally, surface EMG recording is inaccurate in quantitatively assessing muscular strength. Its usefulness maybe limited to biofeedback.

Kato and Kondo, Int. Urogynecol. J. 1997:8; Peattie et al., Brit. J. Obstet Gynaecol., 1988:95; and Wilson and Borland, Aust. N Z J. Obstet. Gynaecol. 1990: 30 showed weighted vaginal cones have also been useful in the assessment and rehabilitation of the pelvic floor. However, Bo, Acta. Obstet. Gynecol. Scand. 1995:74 showed that the cones are often not well accepted and are poorly correlated with physical findings and other pelvic assessment techniques. Hahn et al. demonstrated that women with severe prolapse or incontinence, reduced vaginal tone causes the cones to change position and allows retention in the posterior pelvis without the assistance of the pelvic floor muscles. Contreras Ortiz and colleagues reported on pelvic floor assessment using a modified weighted vaginal cone (the IVD test). The cones were larger than previously used cones, but the same shortcomings were suspected.

Another proposed method for pelvic floor functional assessment is ultrasound of the perineum to measure elevation of the bladder neck during a pelvic contraction. Reddy et al., Am. J. Obstet. Gynecol. 2001:185 showed this method to be useful as a biofeedback device because it discriminates between straining and a contraction; however, quantification of the strength of the pelvic floor contraction is not a possibility.

Finally, the least expensive method to assess pelvic floor muscular strength is digital palpation. Worth et al. and Brink et al. devised numerous scales, which have been shown to have good intra- and inter-observer reliability. This method, however, is limited because it is an indirect measurement of pressure, although some scales have attempted to overcome this shortcoming by including perineal lift as part of the assessment. It is also subjective, which has restricted its usefulness. Nonetheless, the speed and ease of use distinguish it between other currently accepted methods and are the reasons it was used for comparison in this study.

The use of spherical intravaginal devices to enhance pelvic floor rehabilitation in the management of genital prolapse has been previously reported by Adamkiewicz et al., Int. Urogynecol J. 2001:12 and Martin et al, Zentralbl. Gynakol. 1994:16 and is also known from the U.S. patent application Ser. No. 09/303,981. The device is conveniently a plastic sphere with a silicon thread attached for easy insertion and removal and is available in 28–44 mm diameter sizes. Women perform pelvic floor exercises with the sphere in the vagina above the level of the levator ani. As the pelvic floor muscles strengthen the likelihood of device expulsion decreases.

BRIEF SUMMARY OF THE INVENTION

The object of the invention is to provide a method for qualitative assessment of pelvic floor muscular strength.

It is also the object of the invention to provide a diagnostic set for carrying out method.

In accordance with a preferred embodiment of the present invention, a device for qualitative assessment of pelvic floor muscular strength comprises a force gauge, a spherical intracavitary device and a linker connecting the spherical device to the force gauge to measure the force necessary to remove the spherical device from the vagina or anus.

In accordance with another preferred embodiment of the present invention, diagnostic set of the invention comprises at least one spherical intracavitary device and a force gauge, said device and said force gauge being equipped with means allowing attachment of said force gauge to said device after insertion of said device into vagina or anus.

In accordance with another preferred embodiment of the present invention, a method for qualitative assessment of pelvic floor muscular strength comprises the steps of inserting a spherical intracavitary device into vagina or anus above the level of the levator plate and measuring a force necessary to remove said inserted device from said vagina or anus.

Other objects and advantages will become apparent from the following descriptions, taken in connection with the accompanying drawings, wherein, by way of illustration and example, an embodiment of the present invention is disclosed.

BRIEF DESCRIPTION OF THE DRAWING

The drawing constitutes a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION OF THE PREFERRED EMBODIMENTS

Figure 1:
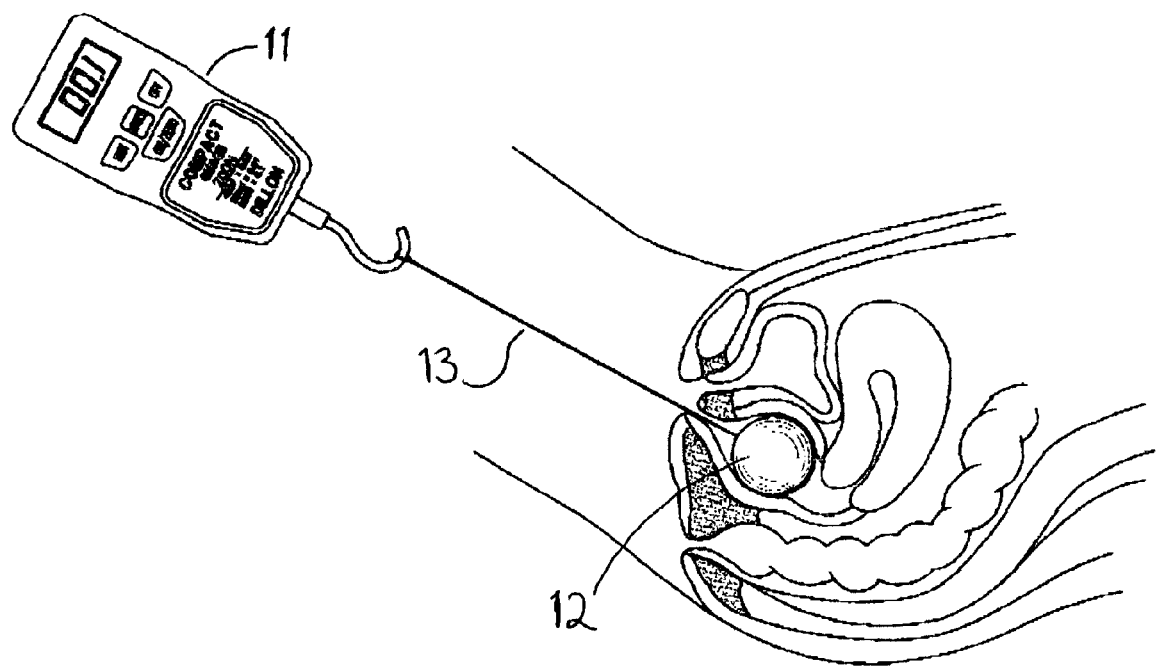
FIG. 1 shows an intracavitary spherical device connected to a force gauge in accordance with a preferred embodiment of the present invention.

Detailed descriptions of the preferred embodiments are provided herein. It is to be understood, however, that the present invention maybe embodied in various forms. Various aspects of the invention may be inverted, or changed in reference to specific part shape and detail, part location; i.e., intravaginal or intra-anal, or part composition. Therefore, specific details disclosed herein are not to be interpreted as limiting, but rather as a basis for the claims and as a representative basis for teaching one skilled in the art to employ the present invention in virtually any appropriately detailed system, structure or manner.

In part, the present invention is a method for qualitative assessment of pelvic floor muscular strength in women comprising inserting a spherical intracavitary device into vagina of a woman above the level of the levator plate and measuring a force necessary to remove said inserted device from said vagina. In the method of the invention a woman's retentive ability of the spherical intracavitary device is used to assess pelvic floor muscular strength. The removal of said device is carried out by pulling out in a smooth motion. The force required for such removal, that is the maximum force indicated by the force gauge during such removal, is recorded. The device is inserted into the vagina in the lithotomy position. Such position is convenient as it allows easy standardization of numerical results of the measurement.

In one embodiment of the method the force necessary to remove the device from a vagina is measured in the relaxation state or resting state of pelvic floor muscles.

In another embodiment of the method the force necessary to remove the device from a vagina is measured during maximum contraction of pelvic floor muscles.

In yet another embodiment of the method the force necessary to remove the device from a vagina both in the relaxation state of pelvic floor muscles and during maximum contraction of pelvic floor muscles is measured.

The measuring can be performed by a force gauge 11 attachable to the spherical intracavitary device 12 by a linker 13 connected to the device, said linker extending after the insertion besides the vagina to allow attachment of the force gauge.

A method for qualitative assessment of pelvic floor muscular strength in women is also provided and comprises inserting a spherical intracavitary device into vagina of a woman above the level of the levator plate and measuring a force necessary to remove the inserted device from the vagina. Measuring is performed by means of a force gauge attachable to the spherical intracavitary device by a linker connected to the device, the linker extending after insertion besides the vagina to allow attachment of the force gauge.

A method for qualitative assessment of pelvic floor muscular strength in women according to another preferred embodiment comprises inserting a spherical intracavitary device into vagina of a woman above the level of the levator plate and measuring a force necessary to remove the inserted device from the vagina. Measuring is performed by means of a force gauge attachable to the spherical intracavitary device by a linker connected to the device, the linker extending after insertion besides the vagina to allow attachment of the force gauge, and the force is measured both in the relaxation state of pelvic floor muscles and during maximum contraction of pelvic floor muscles.

Preferably the spherical intracavitary device is a sphere having a diameter of about 36 mm for women, but may range in diameter from about 20 mm to about 44 mm for women. The linker is preferably a non-elastic thread having means for attachment of said force gauge. The linker preferably can have the form of a non-elastic non-elastic rod connected at one end to the device and connectable with its the force gauge. Connection of the rod with the force gauge can be carried out by means of a ring or a loop located on the rod.

In the lithotomy position, the levator ani muscle must contract to retain the spherical device against the resistance generated by the examiner. This action closely simulates the dynamic physiology of the pelvic floor as a supportive structure. Further, the data are digitally recorded in pounds or grams up to three significant digits. This, as well as the simplicity of the method, should reduce subjectivity and inter-observer variation.

Within reason, the rate at which the device is removed does not influence in a critical manner the force measured. As it is the single measure of maximum force generated that is recorded, the effects of different removal rates are likely minimized.

Other factors, such as lubrication, may contribute to bias. It is therefore advantageous to use a small amount of lubricant in order to reduce any significant differences in vaginal moisture, rugations, and estrogenation between subjects.

Also differences in total vaginal length, degree of prolapse, introital caliber, and angle of withdrawal do not influence in a critical manner the force measured in women. The location of maximum retentive force is at the level of the levator muscle and should not be altered by a longer or prolapsed vaginal canal above this point. Likewise, since the device is a sphere, slight changes in the withdrawal angle are not significant.

Another aspect the present invention encompasses a diagnostic set that comprises at least one spherical intracavitary device and a force gauge. The device and the force gauge being equipped with means allowing attaching the force gauge to the device after insertion of the device into vagina or anus.

The means can have a form of a non-elastic thread connected with its one end to said spherical device. After insertion of the device into vagina, said thread can be simply bound to the force gauge.

Said means preferably can have a form of a non-elastic rod connected to one end of said device and connectable with its second end with said force gauge. Connection of the rod with said force gauge can be carried out, for example, by means of a loop or a ring located on the rod. In such case the force gauge will be equipped with a corresponding means, like a hook, for catching the loop or ring.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A method for qualitative assessment of pelvic floor muscular strength comprises the steps of:
    inserting a spherical intracavitary device into the vagina above the level of the levator plate; and
    measuring a force necessary to remove said inserted device from said vagina with a force gauge.

2. The method of claim 1, wherein said device is inserted into said vagina in the lithotomy position.

3. The method of claim 1, wherein said force is measured in the relaxation state of pelvic floor muscles.

4. The method of claim 1, wherein said force is measured during maximum contraction of pelvic floor muscles.

5. The method of claim 1, wherein said force is measured both in the relaxation of pelvic floor muscles and during contraction of pelvic floor muscles.

6. The method of claim 1, wherein said spherical intracavitary device is a sphere having a diameter of about 28 mm to 44 mm.

7. The method of claim 1, wherein said measuring is performed by means of a force gauge attachable to said spherical intracavitary device by a linker connected to said device, said linker after said insertion extending besides the vagina to allow attachment of said force gauge.

8. The method of claim 7, wherein said linker is a thread having means for attachment of said force gauge.

* * * * *